(12) United States Patent
Carstens

(10) Patent No.: US 9,834,774 B2
(45) Date of Patent: Dec. 5, 2017

(54) METHODS AND COMPOSITIONS FOR RAPID SEAMLESS DNA ASSEMBLY

(71) Applicant: Agilent Technologies, Inc., Loveland, CO (US)

(72) Inventor: Carsten Carstens, San Diego, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 147 days.

(21) Appl. No.: 14/620,017

(22) Filed: Feb. 11, 2015

(65) Prior Publication Data

US 2016/0230175 A1    Aug. 11, 2016

(51) Int. Cl.
| | |
|---|---|
| *C12Q 1/68* | (2006.01) |
| *C12P 19/34* | (2006.01) |
| *C12N 15/64* | (2006.01) |
| *C12N 15/10* | (2006.01) |

(52) U.S. Cl.
CPC ......... *C12N 15/64* (2013.01); *C12N 15/1031* (2013.01)

(58) Field of Classification Search
None
See application file for complete search history.

(56) References Cited

U.S. PATENT DOCUMENTS

| | | | |
|---|---|---|---|
| 5,976,846 A | * | 11/1999 | Passmore ............... C12N 15/64 |
| | | | 435/477 |
| 6,261,797 B1 | | 7/2001 | Sorge et al. |
| 8,067,556 B2 | | 11/2011 | Hogrefe et al. |
| 8,685,676 B2 | | 4/2014 | Hogrefe et al. |
| 2010/0286290 A1 | * | 11/2010 | Lohmann ............ C12Q 1/6844 |
| | | | 514/789 |

FOREIGN PATENT DOCUMENTS

WO    WO2014088693    6/2014

OTHER PUBLICATIONS

Gibson et al., "Enzymatic assembly of DNA molecules up to several hundred kilobases" Nature Methods (May 2009) 6(5):343-347.
Quan, et al. "Circular Polymerase Extension Cloning of Complex Gene Libraries and Pathways", PLoS one, 2009, vol. 4, Issue 7, e6441, pp. 1-6.

* cited by examiner

*Primary Examiner* — Young J. Kim

(57) ABSTRACT

Provided herein are methods for assembling DNA fragments employing at least three enzymatic activities: DNA polymerase, flap endonuclease, and DNA ligase. Certain aspects include methods for generating closed circular DNA products, e.g., plasmid vectors, by assembling various DNA fragments having complementary ends that hybridize to one another. The resulting circular products can be introduced into host cells and selected for desired properties. Kits for performing the method are also provided.

19 Claims, 5 Drawing Sheets

FIG. 4

Table 2A

| slot | assignment | assembly 1 | assembly 2 | assembly 3 | assembly 4 | assembly 5 | assembly 6 | total | fraction |
|---|---|---|---|---|---|---|---|---|---|
| 1 | resistance marker | kn^R | kn^R | kn^R | kn^R | kn^R | kn^R | | |
| 2 | bacterial origin of replication | p15A | p15A | p15A | p15A | p15A | p15A | | |
| 3 | expansion slot | XP1 stuffer | XP1 stuffer | XP1 stuffer | XP1 stuffer | XP1 stuffer | XP1 stuffer | | |
| 4 | expansion slot | XP2 stuffer | XP2 stuffer | XP2 stuffer | XP2 stuffer | XP2 stuffer | XP2 stuffer | | |
| 5 | GOI (gene of interest) | lacZ | lacZ | lacZ | lacZ | lacZ | lacZ | | |
| 6 | fusion domain | GST | MBP | his6 | CBP | SBP | his6/dsbA | | |
| 7 | promoter | T7 | tac | rha | trp | tac | rha | | |
| | point mutation[1] | 2/9 | 1/9 | 3/9 | 3/9 | 3/9 | 5/9 | 17/54 | 31.5% |
| | assembly error[2] | 0/9 | 7/9^p | 0/9 | 0/9 | 0/9 | 0/9 | 7/54 | 13.0% |
| | assembly fidelity | 9/9 | 2/9 | 9/9 | 9/9 | 9/9 | 9/9 | 47/54 | 87.0% |
| | total fidelity | 7/9 | 1/9 | 6/9 | 6/9 | 6/9 | 5/9 | 30/54 | 55.6% |

| slot | assignment | assembly 7 | assembly 8 | assembly 9 | assembly 10 | assembly 11 | assembly 12 | total | fraction |
|---|---|---|---|---|---|---|---|---|---|
| 1 | resistance marker | cm^R | cm^R | cm^R | cm^R | cm^R | cm^R | | |
| 2 | bacterial origin of replication | p15A | p15A | p15A | p15A | p15A | p15A | | |
| 3 | expansion slot | XP1 stuffer | XP1 stuffer | XP1 stuffer | XP1 stuffer | XP1 stuffer | XP1 stuffer | | |
| 4 | expansion slot | lacI | lacI | lacI | lacI | lacI | lacI | | |
| 5 | fusion domain | his6 | SBP | CBP | tmx | HA | myc | | |
| 6 | GOI (gene of interest) | lacZ | lacZ | lacZ | lacZ | lacZ | lacZ | | |
| 7 | promoter | T7 | tac | rha | trp | tac | rha | | |
| | point mutation[1] | 1/6 | 1/6 | 0/6 | 0/6 | 0/6 | 0/6 | 2/36 | 5.6% |
| | assembly error[2] | 0/6 | 0/6 | 0/6 | 0/6 | 0/6 | 0/6 | 0/36 | 0.0% |
| | assembly fidelity | 6/6 | 6/6 | 6/6 | 6/6 | 6/6 | 6/6 | 36/36 | 100.0% |
| | over-all fidelity | 5/6 | 5/6 | 6/6 | 6/6 | 6/6 | 6/6 | 34/36 | 94.4% |

FIG. 5

Table 2B

| slot | assignment | assembly 13 | assembly 14 | assembly 15 | assembly 16 | total | fraction |
|---|---|---|---|---|---|---|---|
| 1 | resistance marker | ap^R | ap^R | cm^R | kn^R | | |
| 2 | bacterial origin of replication | colE1 (pUC) | colE1 (pBR) | p15A | p15A | | |
| 3 | expansion slot | XP1 stuffer | XP1 stuffer | yARS | XP1 stuffer | | |
| 4 | expansion slot | lacI | neo^R | LEU2 | XP2 stuffer | | |
| 5 | GOI (gene of interest) | lacZ | lacZ | lacZ | lacZ | | |
| 6 | promoter | T7 | CMV | GAL1 | T7 | | |
| | point mutation^1 | 3/9 | 0/9 | 2/9 | 0/9 | 5/36 | 13.9% |
| | assembly error^2 | 1/9 | 1/9 | 0/9 | 0/9 | 2/36 | 5.6% |
| | assembly fidelity | 8/9 | 8/9 | 9/9 | 9/9 | 34/36 | 94.4% |
| | over all fidelity | 5/9 | 8/9 | 8/9 | 9/9 | 29/36 | 77.8% |

Table 2C

| | Assemblies 1-6 | Assemblies 7-12 | Assemblies 13-16 | total | efficiency |
|---|---|---|---|---|---|
| point mutation^1 | 17/54 | 2/36 | 5/36 | 24/126 | 19.0% |
| assembly error^2 | 7/54 | 0/36 | 2/36 | 9/126 | 7.1% |
| assembly fidelity | 47/54 | 36/36 | 34/36 | 117/126 | 92.9% |
| Total fidelity | 30/54 | 34/36 | 29/36 | 93/126 | 73.8% |

METHODS AND COMPOSITIONS FOR RAPID SEAMLESS DNA ASSEMBLY

BACKGROUND

Assembly of DNA into functional genetic elements is a fundamental aspect of molecular genetics. DNA assembly methods generally require the generation of DNA fragments having defined, compatible ends that are suitable for subsequent joining, or ligation.

Traditionally, compatible end of DNA fragments are generated by the use of restriction enzymes which can be joined together by a DNA ligase. If restriction enzymes leaving protruding ends are used, directional joining of segments containing matching overlaps can be achieved. Traditional cloning methods have several disadvantages. First, due to unproductive side reactions (either circularization of segments by self-ligation or formation of runway concatamers), traditional ligation methods are not very efficient, with the assembly of more than 3 compatible DNA segments into circular vectors especially inefficient. This method also relies on presence of unique restriction sites at particular locations in the precursor DNA molecules from which the DNA fragments to be joined are derived. These sites might not be available, especially if large fragments are combined. In addition, most restriction sites require the presence of a specific sequence at the end of the processed molecule which lead to "scars" after ligations, often interfering with the ultimate goal of seamless assemblies.

To overcome the ligation junction problem, some methods employ the use of type II restriction enzymes that cleave outside of their recognition sequence. These recognition sequences are added to the ends of the combined fragments, usually by PCR. If the restriction enzyme generates staggered ends, the resulting fragments can be combined directionally resulting in "seamless" assemblies. This approach is the basis of the "golden gate" cloning approach, where suitable restriction sites internal to the cloned fragments can be protected from cleavage by introducing methylations during the PCR amplification of the cloned segments (see e.g., U.S. Pat. No. 6,261,797).

In an alternative approach, DNA fragments can be combined using matching "long" overlapping sequences at their ends. If complementary single stranded ends are generated, typically by specifically degrading one of the DNA strands by either a 5' or 3' exonuclease, the combined segments can be annealed to each other. The annealed segments, usually with overlap lengths of 12-13 nucleotides, are introduced into bacterial host cells where the gaps in the annealed DNA are repaired and sealed by the host repair systems. This approach is generally referred to as "ligation independent cloning" or LIC cloning (see e.g., Haun et al., "Rapid, reliable ligation-independent cloning of PCR products using modified plasmid vectors." BioTechniques 13 (4): 515-8 (1992)). In a variant of this approach known as "Gibson assembly" (see e.g., Gibson et al., "Enzymatic assembly of DNA molecules up to several hundred kilobases." Nature Methods 6 (5): 343-345 (2009)), matching 3'-protruding ends are generated using a 5'-exonuclease. The annealing products are then repaired using a non-strand-displacing DNA polymerase and a ligase to seal potential gaps, thus recreating in vitro some of the host repair processes utilized during LIC-cloning.

A different, overlap dependent assembly method is based on assembly of DNA segments with overlapping ends using a thermal cycling protocol. This process referred to a CPEC assembly (see e.g., Quan, J., and Tian, J. "Circular Polymerase Extension Cloning of Complex Gene Libraries and Pathways." PLoS ONE 4(7): e6441 (2009)) resembles a PCR reaction where the overlaps of the DNA sequences act as primer. The general drawback of this approach is that the amplification process never results in a closed circular product as is required for most bacterial plasmids. When circular permutated overlapping ends are utilized, the typical products are long concatemers. Formation of circular plasmids most likely results from overlapping, off-set intermediates with protruding single stranded ends that are repaired by the host cell. However, due to their structure, these are not easily taken up by the bacterial host, especially when large construct are assembled. Another disadvantage is that larger constructs also require very long cycling protocols.

As such, there exists a need for high efficiency DNA assembly methods and compositions for performing such methods.

SUMMARY

Aspects of this disclosure provide methods for efficient seamless assembly of multiple isolated DNA fragments, e.g., into a replication competent plasmid. As will be evident from the description below, advantages of aspects of the present disclosure include that no processing of the overlapping ends is required prior to assembly to produce covalently closed circular DNA molecules. Further, DNA assembly is largely independent of the size of the assembled vector, allowing the assembly of seven or more fragments within 15 minutes.

Thus, provided herein are methods for assembling DNA fragments employing at least three enzymatic activities: DNA polymerase, flap endonuclease, and DNA ligase. While there are a wide variety of applications for the disclosed methods, certain aspects include methods for generating closed circular DNA products, e.g., plasmid vectors, by assembling various DNA fragments containing complementary ends that hybridize to one another. The resulting circular products can be introduced into host cells which are selected for desired properties, e.g., using a selectable marker cassette present in the one of the DNA fragments (and thus present in the closed circular plasmid produced form the DNA fragments). Many selection criteria can be used, including antibiotic resistance, expression of a reporter gene, etc. Kits for performing the method are also provided.

Certain aspects of the present disclosure are drawn to DNA assembly methods comprising: (a) obtaining at least two DNA fragments, wherein the at least two DNA fragments comprise ends that can selectively hybridize with one another; and (b) contacting the at least two DNA fragments with: (i) a DNA polymerase; (ii) a flap endonuclease; and (iii) a DNA ligase; under reaction conditions that promote hybridization of the at least two DNA fragments and support the activities of components (i), (ii) and (iii), to produce a product comprising an assembled circular DNA comprising at least a portion of each of the at least two DNA fragments.

In certain embodiments, the method further comprising performing at least one thermal cycling incubation step after the contacting step (b), where in some instances multiple thermal cycling incubations steps are performed.

In certain embodiments, the at least two DNA fragments comprise one or more cassettes selected from the group consisting of: one or more selectable marker cassettes, one or more origin of replication cassette, one or more additional functional cassettes, one or more target cassettes, and combinations thereof. In certain embodiments, the one or more functional cassettes are selected from the group consisting of: promoter cassettes, N-terminal purification tag cassettes, C-terminal purification tag cassettes, shuttle origin of replication cassettes, terminator cassettes, protein expression enhancer cassettes, and shuttle selectable marker cassettes. In certain embodiments, the one or more target cassettes comprises a polynucleotide sequence encoding a polypeptide or a regulatory RNA.

In certain embodiments, at least three DNA fragments comprising ends that can selectively hybridize with one another are obtained in step (a), where the product produced comprises an assembled circular DNA comprising at least a portion of each of the at least three DNA fragments. In certain embodiments, at least five DNA fragments comprising ends that can selectively hybridize with one another are obtained in step (a), where the product produced comprises an assembled circular DNA comprising at least a portion of each of the at least five DNA fragments.

In certain embodiments, the assembled circular DNA is a plasmid vector comprises an origin of replication for a bacterial host cell, a selectable marker cassette, and an expression cassette for a gene of interest.

In certain embodiments, the ends of the at least two DNA fragments that can selectively hybridize are at least 20 nucleotides in length. In some embodiments, the ends of the at least two DNA fragments that can selectively hybridize have a $T_m$ of at least 45° C.

In certain embodiments, the DNA polymerase is thermostable, e.g., a DNA polymerase selected from the group consisting of: Pfu DNA polymerase SSO7 fusion, Pfu DNA polymerase, Tma DNA polymerase, Tli DNA polymerase, KOD DNA polymerase, JDF-3 DNA polymerase, PGB-D DNA polymerase, Tgo DNA polymerase, and *Pyrolobus furmarius* DNA polymerase.

In certain embodiments, the flap endonuclease is thermostable, e.g., a flap endonuclease selected from the group consisting of: Pfu FEN-1 and Dna2.

In certain embodiments, the DNA ligase is thermostable, e.g., a DNA ligase selected from the group consisting of: Pfu DNA ligase, Tth DNA ligase, Taq DNA ligase, *Thermus filiformis* ligase, *Rhodothermus marinus* DNA ligase, *Thermus scotoductus* DNA ligase, and *Bacillus stearothermophilus* DNA ligase. In certain embodiments, the DNA polymerase is a non strand-displacing DNA polymerase.

In certain embodiments, the method further comprises introducing the product of step (b) into a host cell and selecting a host cell that harbors the assembled circular DNA, e.g., based on the presence of a selectable marker and/or a reporter gene cassette present in the assembled DNA product.

Additional methods are also provided, as detailed below, as are compositions and kits for performing the methods provided herein.

BRIEF DESCRIPTION OF THE FIGURES

The skilled artisan will understand that the drawings, described below, are for illustration purposes only. The drawings are not intended to limit the scope of the present teachings in any way.

FIG. 4. Table 2A of the disclosure, showing results of a seven fragment assembly reaction according to aspects of the present disclosure (described in detail in the Examples section below).

FIG. 5. Table 2B of the disclosure, showing results of a six fragment assembly reaction according to aspects of the present disclosure, and Table 2C of the disclosure, summarizing the results of Tables 2A and 2B (described in detail in the Examples section below).

Figure 1:
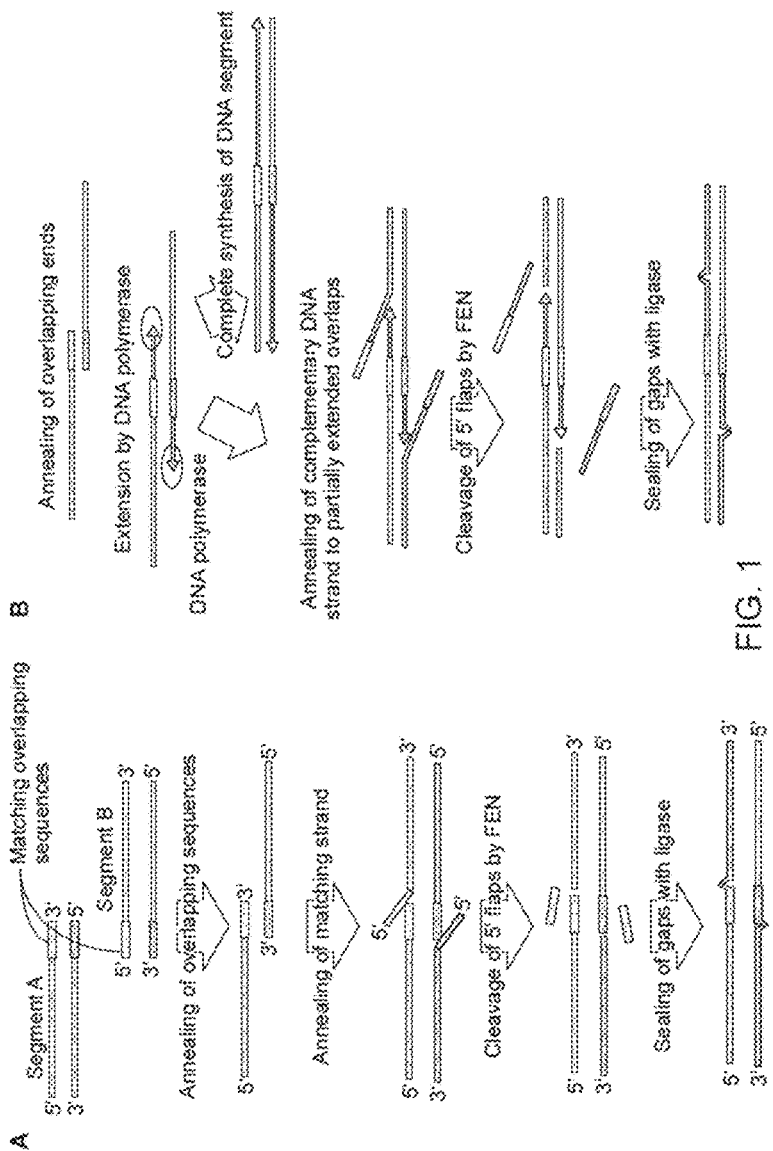
FIG. 1. Generation of covalently linked DNA using FEN, DNA ligase and DNA polymerase. Panel A shows a schematic of a method according to aspects of the present disclosure for linking two dsDNA segments by a flap endonuclease (FEN) and a DNA ligase. FEN recognizes 5'-Flaps of at least 3 nucleotides and cleaves the Flap, leaving a gap that can be closed by DNA ligase. Panel B shows a schematic of a method according to aspects of the present disclosure for inclusion of a DNA polymerase in addition to the FEN and DNA ligase in an assembly reaction as describe herein. The reaction results in either complete synthesis of the annealed segment or partial extension followed by FEN/DNA ligase mediated joining to the matching displaced DNA strand.

The following legend is for superscripts in Tables 2A, 2B and 2C:
1) point mutation defined as base substitutions or single base deletions;
2) assembly errors defined as missing segments or large deletions including one segment or cloning junction;
   a) all assembly errors affect the MBP segment.

Abbreviations in Table 2A, 2B, and 2C: $ap^R$, ampicillin resistance marker; $cm^R$, chloramphenicol resistance marker; $kn^R$, tn903 kanamycin resistance marker; T7, bacteriophage T7 gene10 promoter; CMV, immediate early promoter from the cytomegalo virus; yARS, yeast autonomous replicating sequence, plasmid origin of replication in yeast; $neo^R$, eukaryotic expression cassette for the tn5 kanR marker, provides resistance to neomycin in mammalian cells; LEU2, yeast autotrophy marker, complements leucine requirement in minimal media; SBP, streptavidin binding peptide; CBP, calmodulin binding peptide; MBP, maltose binding peptide; HA, hemaglutinine binding peptide domain; thrx, thioredoxin; tac, IPTG inducible promoter; rha, rhamnose BAD promoter, trp, typtophane inducible promoter.

DEFINITIONS

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a cassette" refers to one or two or more cassettes, i.e., a single cassette and multiple (at least two) cassettes. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotides from about 2 to 200 nucleotides, up to 500 nucleotides in length. Oligonucleotides may be synthetic or may be made enzymatically, and, in some embodiments, are 4 to 150 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51 to 60, 61 to 70, 71 to 80, 80 to 100, 100 to 150 or 150 to 200 nucleotides in length, for example.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long enough to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15 to 25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence of the strand to hybridize therewith and thereby form the template for the synthesis of the extension product.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction (or under hybridizing reaction conditions). The hybridization reaction can be made to be highly specific by adjustment of the hybridization conditions (often referred to as hybridization stringency) under which the hybridization reaction takes place, such that hybridization between two nucleic acid strands will form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "Selectively hybridizable" to a reference nucleic acid sequence if the two sequences specifically hybridize to one another under moderate to high stringency hybridization and/or wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42° C. in 50% formamide, 5×SSC, 5×Denhardt's solution, 0.5% SDS and 100 µg/mL denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula: $T_m=81.5+16.6(\log_{10}[Na^+])+0.41$ (fraction G+C)−(60/N), where N is the chain length and $[Na^+]$ is less than 1 M. See Sambrook and Russell (2001; Molecular Cloning: A Laboratory Manual, $3^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

The term "free in solution," as used here, describes a molecule, such as a polynucleotide, that is not bound or tethered to another molecule.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "ligating", as used herein, refers to the enzymatically catalyzed joining of the terminal nucleotide at the 5' end of a first DNA molecule to the terminal nucleotide at the 3' end of a second DNA molecule.

The term "covalently linking" refers to the production of a covalent linkage between two separate molecules, e.g., Ligating is a type of covalent linking.

The terms "set" and "plurality" are used interchangeably to refer to a population that contains at least 2 members. In certain cases (and depending on the context), a plurality or a set may have at least 3, at least 4, at least 5, at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

The term "digesting" is intended to indicate a process by which a nucleic acid is cleaved by a restriction enzyme. In order to digest a nucleic acid, a restriction enzyme and a nucleic acid containing a recognition site for the restriction enzyme are contacted under conditions suitable for the restriction enzyme to work. Conditions suitable for activity of commercially available restriction enzymes are known, and supplied with those enzymes upon purchase.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "extending", as used herein, refers to the extension of a primer by the addition of nucleotides using a polymerase. If a primer that is annealed to a nucleic acid is extended, the nucleic acid acts as a template for the extension reaction.

The term "do not hybridize to each other", as used herein in the context of nucleic acids that do not hybridize to each other, refers to sequences that have been designed so that they do not anneal to one another under stringent conditions. Exemplary sequences that do not hybridize with each other (which may be called "sequence tokens" in certain publications), are described in, e.g., US20070259357 and Brenner et al (Proc. Natl. Acad. Sci. 1992 89:5381-3), which are incorporated by reference herein.

The terms "that hybridize to each other", as used herein in the context of nucleic acids that hybridize to one other, refers to sequences that been designed so that they anneal to one another under stringent conditions.

As used herein, the term "flap cleavage reaction" refers to a reaction in which a substrate is cleaved in an overlap-dependent manner by a flap endonuclease to release a flap. The principles of flap assays are well known and described in, e.g., Lyamichev et al. (Nat. Biotechnol. 1999 17:292-296), Ryan et al (Mol. Diagn. 1999 4:135-44) and Allawi et al (J Clin Microbiol. 2006 44: 3443-3447).

The term "flap endonuclease" or "FEN" for short, as used herein, refers to a class of nucleolytic enzymes that act as structure specific endonucleases on DNA structures with a duplex containing a single stranded 5' overhang, or "flap", on one of the strands that is displaced by another strand of nucleic acid, i.e., such that there are overlapping nucleotides at the junction between the single and double-stranded DNA. FENs catalyze hydrolytic cleavage of the phosphodiester bond at the junction of single and double stranded DNA, releasing the overhang, or the flap. Flap endonucleases are reviewed by Ceska and Savers (*Trends Biochem. Sci.* 1998 23:331-336) and Liu et al (*Annu. Rev. Biochem.* 2004 73: 589-615). FENs may be individual enzymes, multi-subunit enzymes, or may exist as an activity of another enzyme or protein complex, e.g., a DNA polymerase. A flap endonuclease may be thermostable (e.g., Pfu FEN).

The term "flap endonuclease substrate", as used herein, refers to a nucleic acid complex that can be cleaved by a flap endonuclease to produce cleavage products. Such complex contains a single stranded 5' overhang (a "flap") that has been displaced by another strand in a duplex.

The term "cassette" refers to a double stranded DNA molecule that, when present in a construct in an appropriate context, is functional or encodes a product of interest. Promoters, terminators, origins of replication and coding sequences are examples of cassettes. Cassettes are modular in the sense that they are functional when they are moved into an equivalent context in one or more different constructs. For example, a promoter (which is a type of cassette) can be moved from one construct to another and can drive the expression of different coding sequences. Likewise, coding sequence can be transcribed by various upstream promoters. A cassette can be made by PCR or synthesized by any other method. In some, but not all cases, a cassette can contain more than one functional element in operable linkage. For example, a promoter cassette may also contain a 5' untranslated region, a ribosome binding site and a terminator in addition to the sequence of interest. In addition, an expression cassette may contain a promoter, a transcriptional start site, a coding sequence of interest, and a transcriptional terminator in operable linkage such that the gene of interest is expressed when present in a desired host cell. One or more DNA cassettes can be present in a DNA fragment that finds use in the disclosed methods (e.g., having ends that can selectively hybridize with another DNA fragment).

The term "coding sequence" refers to a sequence that encodes a polypeptide and to a sequence that encodes a functional RNA, e.g., a regulatory RNA.

The term "set" within the context of a "set of cassettes" refers to a group of at least two cassettes (e.g., 2, 3, 4, 5, or 6 or more cassettes) that are functionally related. For example, one set of cassettes may contain different promoters, another set of cassettes may contain different terminators, another set of cassettes may contain different selectable markers, and a further set of cassettes may contain different origins of replication, and so on.

The term "set of origin of replication cassettes" refers to cassettes that contain origins of replication, where each cassette contains a single origin of replication and the different origin of replication cassettes contain different origins of replication. A set of origin of replication cassettes may in certain cases contain one or more of a bacterial origin of replication cassette (which may result in a high or low copy number), a yeast origin of replication cassette and a mammalian origin of replication cassette.

The term "set of selectable marker cassettes" refers to cassettes that encode selectable markers (i.e., proteins that can be used to select cells that contain the protein), where each cassette encodes a single selectable marker and the different selectable marker cassettes contain different selectable markers. A selectable marker of replication cassettes may contain one or more bacterial selectable marker cassettes, one or more yeast selectable marker cassettes and/or one or more mammalian selectable marker cassettes. Exemplary selectable markers encode proteins that provide resistance to antibiotics such as ampicillin, for example.

The term "target cassette" refers to a cassette that comprises a sequence of interest. In some cases the target cassette encodes a product (e.g., a protein or RNA product) that is to be expressed in a cell, e.g., by operably linking the target cassette to at least a promoter. In this context, the term "sequence of interest" is intended to include a sequence or series of sequences of interest. A single sequence of interest may code for a specific protein desired for large scale expression and purification. A series of sequences may result in expression of a number of proteins that, in certain cases, may convert a starting substrate into a final product of interest, such as a fine chemical intermediate, an antibiotic or derivative thereof, a portion of or an entire anabolic or catabolic pathway, or a specific transcriptional circuit, as examples.

The term "set of functional cassettes" refers to cassettes that are functionally related. As will be described in greater detail below, types of functional cassette include, but are not limited to: promoter cassettes, terminator cassettes, shuttle selectable marker cassettes (i.e., a second cassette that can be added to a plasmid in addition to a first origin of replication cassette to allow the plasmid to replicate in another species), and protein coding regions including cassettes that encode N-terminal purification tags, C-terminal purification tags, protein expression enhancers, counter selectable markers and reporter proteins, etc.

The term "vessel" refers to any type of container, e.g., a tube or vial. In this context, the different wells of a multi-well plate (e.g., a 96-well plate) should be considered different vessels.

The term "selecting" refers to the act of obtaining an item from a plurality based on at least one criterion. For example, a transformed host cell containing a plasmid of interest can be selected from host cells that do not contain the plasmid by using a selectable marker present on the plasmid, e.g., a marker for antibiotic resistance.

The term "cassettes comprise ends that hybridize with one another to produce a circular product" refers to a collection of cassettes that contain ends that are designed to hybridize with each other in a way that provides a circular DNA molecule that contains the collection of cassettes.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter).

The terms "transformed" and "transfected" refer to the introduction of exogenous nucleic acid into a host cell to yield a plasmid or other vector that autonomously replicates in the host cell. Electroporation, heat shock, viral infection, and chemical (e.g., liposome-mediated) means, as well as other means (e.g., injection, dipping, etc., for plant) are exemplary ways in which a cell can be transformed or transfected by an exogenous nucleic acid.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

As summarized above, provided herein are methods for assembling DNA fragments employing at least three enzymatic activities: DNA polymerase, flap endonuclease, and DNA ligase. The activities of these enzymes in joining DNA fragments is exemplified in FIG. 1.

In FIG. 1 Panel A, two DNA fragments (segment A and segment B) have matching overlapping sequences that anneal to one another when placed under reaction conditions that promote hybridization (also referred to herein as "ends that can selectively hybridize with one another"). When the matching strands for the DNA fragments anneal, "flaps" are formed (i.e., 5' single stranded regions adjacent to a double stranded region) that are substrates for cleavage by a FEN enzyme. DNA ligase can then join the ends forming a single DNA product containing both DNA fragments. FIG. 1 Panel B shows another example in which two DNA fragments are annealed and either fully extended by DNA polymerase (right path; which forms a single DNA product containing the two DNA fragments) or annealed and partially extended, forming flap structures similar those in FIG. 1 Panel A. FEN cleavage and DNA ligation in this path results in the desired single DNA product.

Based on these enzymatic activities (DNA polymerase, flap endonuclease, and DNA ligase), certain aspects of the present disclosure provide a DNA assembly method that includes: obtaining at least two DNA fragments containing ends that can selectively hybridize with one another, and contacting the at least two DNA fragments with (i) a DNA polymerase; (ii) a flap endonuclease; and (iii) a DNA ligase, under reaction conditions that promote hybridization of the at least two DNA fragments and support the activities of components (i), (ii) and (iii), to produce a product that has therein an assembled circular DNA that has at least a portion of each of the at least two DNA fragments.

In some embodiments, the end sequences that can selectively hybridize can be in the range of 4 to 100 base pairs, e.g., 10 to 80, 15 to 50, 20 to 40 base pairs in length and should not hybridize to any non-end sequences in any of the fragments or to any end sequence of DNA fragments that are not intended to be joined together (or directly assembled with one another). In certain embodiments, the ends of the at least two DNA fragments that can selectively hybridize are at least 4 nucleotides in length, e.g., at least 5, 10, 15, 20, 25, 30, 35, 40 nucleotides in length. In certain cases, the end sequences may contain other features as desired, such as restriction sites, primer binding sites and/or T7/T3 promoters that may facilitate future manipulations after several DNA fragments have been assembled (see description below of examples of specific cassettes that find use in DNA fragments). In particular cases, the end sequences that are intended to be hybridized (and thus joined) are $T_m$-matched, where the term "$T_m$-matched" refers to a set of sequences that have $T_m$'s that are within a defined range, e.g., within 2° C., 5° C., 8° C. or 10° C. of one another. In some embodiments, the ends of the at least two DNA fragments that can selectively hybridize have a $T_m$ of at least 30° C., e.g., at least 35° C., 40° C., 45° C., 50° C., 55° C., 60° C., 65° C., 70° C., or 75° C.

Figure 2:
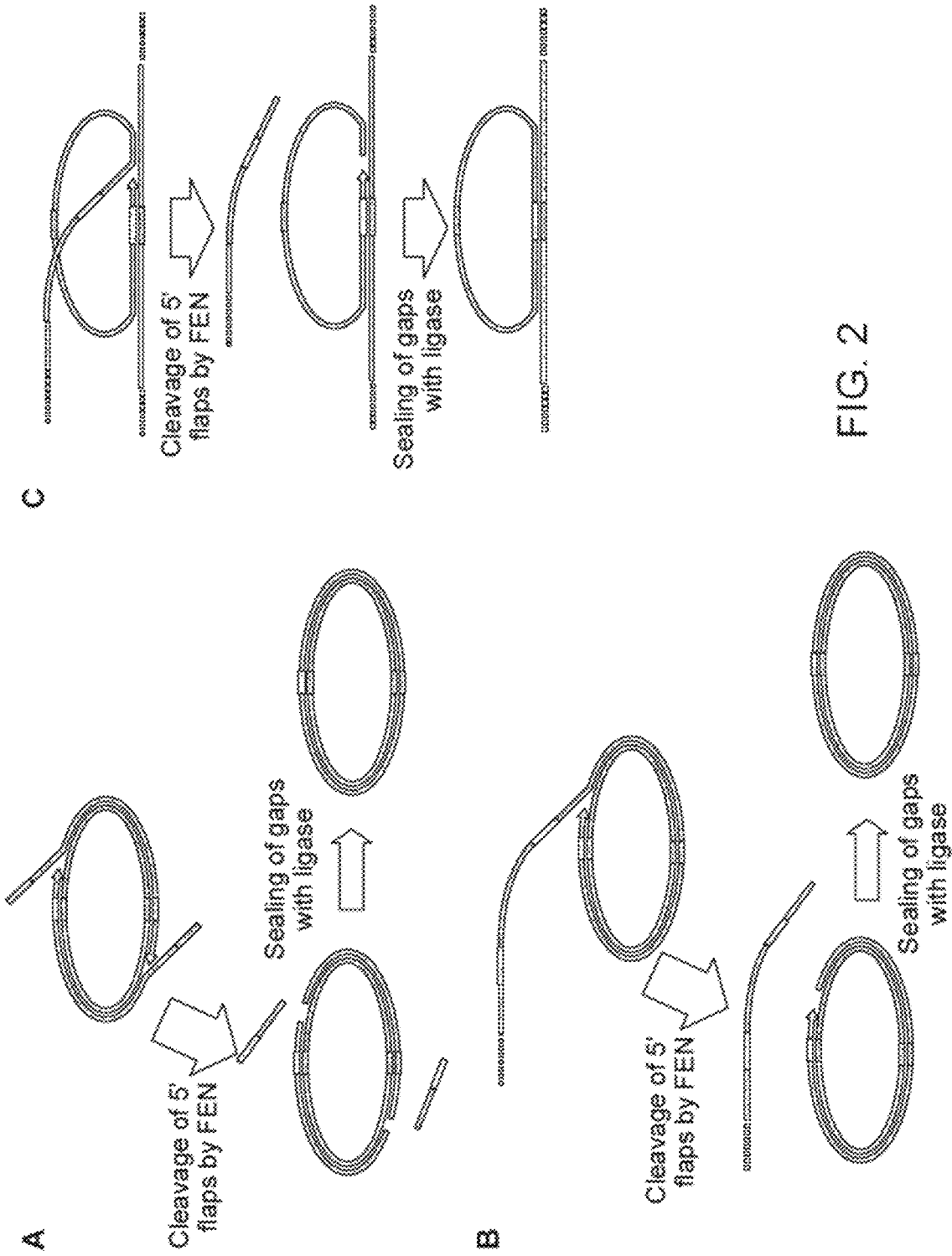
FIG. 2. Formation of covalently closed, circular plasmids by FEN and DNA ligase activity. Panel A shows a schematic of a method according to aspects of the present disclosure for assembling a circular plasmid from mutual annealing of the hybridizable ends generating cleavable overlaps. Panel B shows a schematic of a method according to aspects of the present disclosure for generating a circular plasmid from the end of a concatemer using a circular annealing template. Panel C shows a schematic of a method according to aspects of the present disclosure for generating a closed circular plasmid from the 3' end of a concatemer using a second, complementary concatemer as the annealing template. For clarity, only a two fragment plasmid assembly is shown (assembly of more than two DNA fragments into circular products is described below and demonstrated in the Examples).

In some embodiments, the ends of DNA fragments to be joined can be hybridized to a template polynucleotide that defines the joining region. Templates can be any desired length, including, as shown in FIG. 2 Panel B, the full length of a desired DNA product (e.g., a circular DNA product). Template DNAs are designed to (1) hybridize to at least the hybridizable ends of a least two DNA fragments to be joined and (2) generate substrates that can be acted upon by the enzymes in the reaction (FEN, DNA polymerase and DNA ligase) resulting in joining of the hybridized DNA fragments. A reaction can include any number of template polynucleotides, e.g., 1, 2, 3, 4, 5, 6, 7, 8, 9, 10, or more. In some embodiments, there is a template polynucleotide for each desired DNA fragment joining event, while in other embodiments only a subset of the desired DNA fragment joining events use templates.

The design of the ends of each DNA fragment will depend on the desired orientation and order of the DNA fragments in the desired DNA product (e.g., a circular plasmid). Thus, in some embodiments, each DNA fragment contains a first sequence of nucleotides at one end and a second sequence of nucleotides at the other end where the sequences at the first and second ends are different from one another and where the combination of sequences at the ends of the different DNA fragments are designed to produce a desired product (e.g., a chain of joined DNA fragments, which can be either linear product or in the form of a closed circular product).

One example is shown in FIG. 2 Panel A. This figure shows a schematic of a method according to aspects of the present disclosure for assembling a closed circular product, e.g., a plasmid, from two DNA fragments. The first and second DNA fragments have ends that are designed to hybridize to one another to form a circular structure with two flaps that can be cleaved by FEN and sealed with DNA ligase. In this example, each of the first and second DNA fragments have "a" and "b" sequences at opposite ends, where like sequences can hybridize to one another. This general DNA fragment design can be modified to include 3, 4, 5, 6, 7, 8, 9 or 10 or more DNA fragments having selectively hybridizable ends. Under appropriate reaction conditions, and in the presence of/when contacted with a FEN, a DNA polymerase and a DNA ligase, the DNA fragments are joined to form a circular DNA product having all, or at least a portion, or each of the DNA fragments (as detailed herein). [It is noted that covalently closed circles can also be formed by direct circularization of a single DNA fragment having the same selectively hybridizable sequence at both ends (i.e., a and a).]

One example of a multiple DNA fragment method includes obtaining a first DNA fragment (1) having sequence a at one end and sequence b at the other, a second DNA fragment (2) having sequence b at one end and sequence c at the other, and a third DNA fragment (3 having a c at one end and sequence a at the other and placing them under reaction conditions for selective hybridization and in the presence of a DNA polymerase, a FEN, and a DNA ligase. The orientation of hybridizable ends (i.e., where like-lettered ends of different DNA fragments hybridize to one another under hybridization reaction conditions) will then form a circular DNA product having the following order of DNA fragment joining: 1 joined to 2 (via sequence b), 2 joined to 3 (via sequence c), and 3 joined to 1 (via sequence a). As noted, the general principle described can be expanded to include more DNA fragments (e.g., a total of 4, 5, 6, 7, 8, 9 or 10 or more fragments). In these examples, each end of a DNA fragment hybridizes with only one end of a different DNA fragment in the reaction. However, a user may include DNA fragments where a first DNA fragment has an end that can hybridize to the end of two other DNA fragments in the reaction. In these situations, multiple possible DNA products can be generated, one or more of which the user may want to select (e.g., a user may want to include multiple DNA fragments with different promoter cassettes in each to generate a multiple different expression plasmids each with a different promoter).

It is noted here that due to the competing annealing of the matching displaced strand with the overlapping ends, a single cycle of melting, annealing and joining is often not 100% effective. As such, repeated cycles improve coupling yields. Therefore, the use of heat stable FEN endonucleases and DNA ligases is preferred (although not necessary, as methods that employ with immobilized mesophilic DNA ligases and FEN are envisioned, e.g., microfluidics-based methods). Therefore, in certain embodiments of the disclosure, multiple thermal cycling incubations steps are performed (e.g., from 2 to 10 cycles, e.g., at least 3, 4, 5, 6, or 7).

In certain embodiments, the at least two DNA fragments comprise one or more cassettes having a specific function or property. Cassettes can be selected from the group consisting of: one or more selectable marker cassettes, one or more origin of replication cassette, one or more additional functional cassettes, one or more target cassettes, and combinations thereof. In certain embodiments, the one or more functional cassettes are selected from the group consisting of: promoter cassettes, N-terminal purification tag cassettes, C-terminal purification tag cassettes, shuttle origin of replication cassettes, terminator cassettes, protein expression enhancer cassettes, and shuttle selectable marker cassettes.

While each of the cassettes notes above would be understood by those of ordinary skill in the art, a brief description of several is provided below.

An origin of replication cassette allows the plasmid to replicate in one species (e.g., *E. coli*), while a shuttle origin of replication cassette allows the same plasmid to replicate in another species cells (e.g., yeast or mammalian cells, for example). Cassettes encoding solubility enhancing tags and/or purification tags include those for GST, MBP and NusA (among many others) which can be under the control of a variety of different promoters (prokaryotic and eukaryotic). A target cassette can include a coding sequence for a polypeptide or a regulatory RNA, e.g., a ribozyme or a small RNA such as a miRNA or siRNA.

Any of a variety of DNA polymerases find use in the methods of the present disclosure, including thermostable DNA polymerases, e.g., Pfu DNA polymerase SSO7 fusion, Pfu DNA polymerase, Tma DNA polymerase, Tli DNA polymerase, KOD DNA polymerase, JDF-3 DNA polymerase, PGB-D DNA polymerase, Tgo DNA polymerase, and *Pyrolobus furmarius* DNA polymerase. In certain embodiments, the DNA polymerase is a non-strand-displacing DNA polymerase, whereas in other embodiments, the DNA polymerase is a strand-displacing polymerase.

Any of a variety of flap endonucleases (FENs) find use in the methods of the present disclosure, including thermostable FENs, e.g., Pfu FEN-1 and Dna2.

Any of a variety of DNA ligases find use in the methods of the present disclosure, including thermostable DNA ligases, e.g., Pfu DNA ligase, Tth DNA ligase, Taq DNA ligase, *Thermus filiformis* ligase, *Rhodothermus marinus* DNA ligase, *Thermus scotoductus* DNA ligase, and *Bacillus stearothermophilus* DNA ligase.

In certain embodiments, the method further comprises introducing the DNA assembly product into a host cell and selecting a host cell that harbors the assembled circular DNA, e.g., based on the presence of a selectable marker and/or a reporter gene cassette present in the assembled DNA product. Introduction of DNA into host cells can be performed by any convenient method, many of which are routine in the art, e.g., by transformation. Exemplary hosts include prokaryotic and eukaryotic cells, e.g., monera (unicellular and colonial—including the true bacteria [eubacteria] and cyanobacteria [blue-green algae]); protista (unicellular protozoans and unicellular & multicellular [macroscopic] algae with 9+2 cilia and flagella called undulipodia); fungi (haploid and dikaryotic [binucleate] cells, multicellular, generally heterotrophic, without cilia and eukaryotic (9+2) flagella [undulipodia]); plantae (haplodiploid life cycles, mostly autotrophic, retaining embryo within female sex organ on parent plant)' and animalia (multicellular animals, without cell walls and without photosynthetic pigments, forming diploid blastula. In general terms, the selectable marker cassette and the origin of replication cassettes are selected so as to be compatible with the host cell used. For example, the selectable marker cassette and the origin of replication cassettes included should function so that once the assembled DNA product is introduced into the desired host cell, these cassettes allow the host cell to survive antibiotic treatment and can allow the plasmid to replicated in the host cell. One or more further rounds of screening may be performed by testing for the expression of a reporter gene (e.g., a fluorescent protein), by PCR screening of colonies, or by purifying plasmid DNA using a "mini-prep" procedure followed by restriction enzyme digestion and/or sequencing.

Kits

Also provided by this disclosure is a kit for practicing the subject method, as described above. A subject kit may contain one or more DNA fragments, e.g., DNA fragments containing cassettes of interest, e.g., one or more origin of replication cassettes; one or more selectable marker cassettes; one or more functional cassettes; one or more target cassettes; etc. The DNA fragments can be provided in different vessels. In some embodiments, a user of the kit provides a DNA fragment containing a target cassette, e.g., a gene of interest.

In addition to the cassettes, a kit may also contain reagents, e.g., buffers, enzymes and other necessary reagents, for performing the method described above. The various components of the kit may be present in separate containers or certain compatible components may be pre-combined into a single container, as desired.

In addition to the above-mentioned components, the subject kits may further include instructions for using the components of the kit to practice the subject methods and instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Some abbreviations are found in this disclosure: glutathione-S transferase (GST), maltose binding protein (MBP), cellulose binding protein (CBP), polymerase chain reaction (PCR), peptide nucleic acid (PNA), ribonucleic acid (RNA) and deoxyribonucleic acid (DNA). Other abbreviations are explained in the text.

Although the foregoing embodiments have been described in some detail by way of illustration and example for purposes of clarity of understanding, it is readily apparent to those of ordinary skill in the art in light of the above teachings that certain changes and modifications can be made thereto without departing from the spirit or scope of the appended claims.

EXAMPLES

Aspects of the present teachings can be further understood in light of the following examples, which should not be construed as limiting the scope of the present teachings in any way.

EXAMPLE 1

Enzymatic Activities for Ordered Assembly of a Replication Competent Plasmid from 7 Segments Containing Specifically Targeted Overlapping Ends dsDNA fragments for assembly were generated by PCR using primer with 15-20 nucleotides of 5'-extensions matching the 3'end of the intended coupling segment, generating 30-40 bps matching overlapping ends with the coupling target segment. The products of the PCR reactions were digested with DpnI to destroy the template plasmids prior to purification. All template plasmids with exception for segment containing the replication origin were amplified from plasmids containing a conditional R6K origin that is not replication competent in standard cloning hosts. The assembly reactions were carried out in a 25 ul reaction volume containing using 50 nM of each DNA fragment, 2U of Pfu DNA polymerase SSO7 fusion (Agilent), 400 ng Pfu FEN1 (Agilent), 120 U of Tsc DNA ligase, and 2 U of recombinant Pfu polymerase enhancing factor (PEF, Agilent) in 20 mM Tris HCl, 50 mM KCl, 10 mM (NH4)SO4, 200 µM each dNTP, 2 mM MgCl2, 100 nM NAD, 0.1% (v/v) Triton X-100, and 25 µg BSA. For assembly, The DNA segments were melted for 1 minute at 95° C. and ligation reactions were carried out for 8 cycles of 20 seconds at 95° C., 20 seconds at 60° C., and 1 minute at 68° C. One (1) µl of the assembly reaction was used to transform 50 µl of chemically competent XL1-blue cells (Agilent). After 1 h recovery in 500 µl media, 50 µl or 500 µl of the recovery culture were plated on LB plates containing 50 µg/ml ampicillin. The assembled plasmid corresponds to assembly reaction 13 except that a his6 tag segment was added between the T7 promoter and the lacZ ORF.

Figure 3:
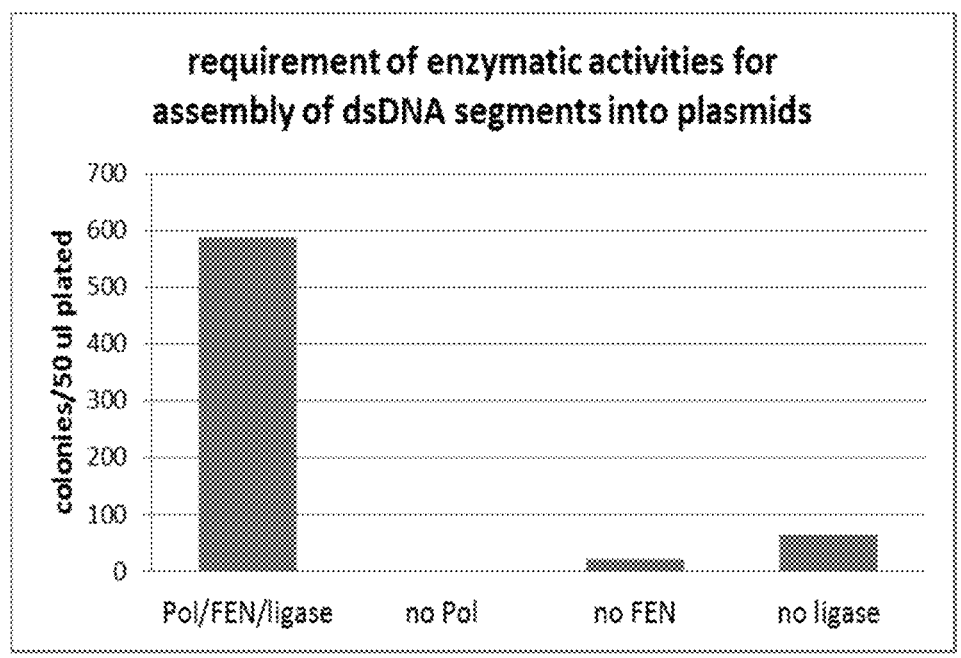
FIG. 3. Synergy of circular DNA assembly using three enzymatic activities. Seven dsDNA segments with matching overlapping ends were assembled into a circular plasmid using DNA polymerase, FEN and DNA ligase as well as enzyme blends lacking one of the enzymes. X11-blue host cells were transformed with 1 µl the assembly reactions and resulting ampicillin resistant colonies were counted. (For experimental details Example 1).

As can be seen in Table 1 below and FIG. 3, an effective multi-segment assembly is most efficient with all three enzymatic activities. Successful assembly is strictly dependent on polymerase activity whereas omission of either FEN or DNA ligase results in a 27-fold or 9-fold drop in efficiency, respectively. While not being bound by theory, the requirement for DNA polymerase activity is likely due to its ability to stabilize annealing events by extending the annealed ends or, for short DNA segments, due to the complete extension the annealed overlap to the end the segment, which may be faster than the annealing of the complementary strand required for FEN/ligase-based fragment joining. Thus, the process is a hybrid of DNA polymerization and end joining by concerted action of FEN and DNA ligase. Schematics of the mixed processes are shown in FIG. 1 Panel B.

TABLE 1 components required for simultaneous assembly of 7 DNA segments

| Enzymes in blend | colonies/50 ul of transformation mix |
|---|---|
| Polymerase + FEN + ligase | 588 |
| FEN + ligase | 0 |
| Polymerase + ligase | 22 |
| Polymerase + FEN | 65 |

EXAMPLE 2

Fidelity of Assembly

To assess the fidelity of the assembly process, 16 different assembly reactions were carried in tree replicates using the protocol described in Example 1. Twelve (12) vectors were assembled from 7 dsDNA segments (FIG. 4; Table 2A) and 4 vectors were assembled from 6 DNA segments (FIG. 5; Table 2B). The specifics of each assembly reaction are detailed in FIGS. 4 and 5 (Tables 2A, 2B and 2C; see Description of Figures section above). From each replicate of each assembly reaction, 3 clones were selected for sequencing resulting in 9 sequenced clones for each assembly. For assemblies 7-12 sequencing reactions failed for technical reasons for 1 replicate and were omitted from the overall analysis. For analysis, errors were characterized either as mutations (base substitutions and singe base deletions) or as assembly errors. Assembly errors were defined as altered order of assembly (none were observed) or large deletions or insertion involving one segment or the cloning junctions. The results are shown in FIGS. 4 and 5 (Tables 2A, 2B and 2C).

The over-all fidelity of the assembly process (the chance that an isolated clone is correct) was 73.8%. Most of the errors (representing 19% of the clones; 24/126) were due to point mutations, the majority of them residing in the primer sequences used to amplify the dsDNA segments. Thus, the observed point mutations appear to reflect the fidelity of the oligonucleotide synthesis process rather than being a consequence of the assembly method. The remainder of the errors, representing 7.1% of the clones (9/126) were classified as assembly errors. The majority of them (7/9) affecting only one dsDNA element (MBP), the other two involving a his6 tag. The assembly errors therefore appear to reflect the specific features of a DNA segment (either DNA sequences or the physical properties of the DNA preparation) rather than a general feature of the assembly process.

The invention claimed is:

1. A DNA assembly method comprising:
   (a) obtaining at least two double-stranded DNA fragments, wherein the at least two double-stranded DNA fragments comprise ends having sequences at opposite ends that can selectively hybridize with one another to form a circular structure comprising the at least two double-stranded DNA fragments; and
   (b) contacting the at least two double-stranded DNA fragments with:
      (i) a DNA polymerase;
      (ii) a flap endonuclease; and
      (iii) a DNA ligase;
   under reaction conditions that promote hybridization of the at least two DNA fragments and support the activities of components (i), (ii) and (iii), wherein the ends of the at least two double-stranded DNA fragments are partially extended by the DNA polymerase to form a 5'-single stranded overhang, the flap endonuclease cleaves the 5'-single stranded overhang forming a circular structure having gaps, and the DNA ligase seals the gaps to produce a product comprising an assembled circular DNA comprising at least a portion of each of the at least two double-stranded DNA fragments.

2. The method of claim 1, further comprising performing at least one thermal cycling incubation step after the contacting step (b).

3. The method of claim 2, wherein multiple thermal cycling incubations steps are performed.

4. The method of claim 1, wherein the at least two double-stranded DNA fragments comprise one or more cassettes selected from the group consisting of: one or more selectable marker cassettes, one or more origin of replication cassette, one or more additional functional cassettes, one or more target cassettes, and combinations thereof.

5. The method of claim 4, wherein the one or more functional cassettes are selected from the group consisting of: promoter cassettes, N-terminal purification tag cassettes, C-terminal purification tag cassettes, shuttle origin of replication cassettes, terminator cassettes, protein expression enhancer cassettes, and shuttle selectable marker cassettes.

6. The method of claim 4, wherein the one or more target cassettes comprises a polynucleotide sequence encoding a polypeptide or a regulatory RNA.

7. The method of claim 1, wherein at least three double-stranded DNA fragments comprising ends that can selectively hybridize with one another are obtained in step (a), and wherein the product produced comprises an assembled circular DNA comprising at least a portion of each of the at least three DNA double-stranded fragments.

8. The method of claim 1, wherein at least five double-stranded DNA fragments comprising ends that can selectively hybridize with one another are obtained in step (a), and wherein the product produced comprises an assembled circular DNA comprising at least a portion of each of the at least five double-stranded DNA fragments.

9. The method of claim 1, wherein the assembled circular DNA is a plasmid vector comprises an origin of replication for a bacterial host cell, a selectable marker cassette, and an expression cassette for a gene of interest.

10. The method of claim 1, wherein the ends of the at least two double-stranded DNA fragments that can selectively hybridize are at least 20 nucleotides in length.

11. The method of claim 10, wherein the ends of the at least two double-stranded DNA fragments that can selectively hybridize have a Till of at least 45° C.

12. The method of claim 1, wherein the DNA polymerase is thermostable.

13. The method of claim 12, wherein the DNA polymerase is selected from the group consisting of: Pfu DNA polymerase SS07 fusion, Pfu DNA polymerase, Tma DNA polymerase, Tli DNA polymerase, KOD DNA polymerase, JDF-3 DNA polymerase, PGB-D DNA polymerase, Tgo DNA polymerase, and *Pyrolobus furmarius* DNA polymerase.

14. The method of claim 1, wherein the flap endonuclease is thermostable.

15. The method of claim 14, wherein the flap endonuclease is selected from the group consisting of: Pfu FEN-1 and Dna2.

16. The method of claim 15, wherein the DNA ligase is thermostable.

17. The method of claim 16, wherein the DNA ligase is selected from the group consisting of: Pfu DNA ligase, Tth DNA ligase, Taq DNA ligase, *Thermus filiformis* ligase, *Rhodothermus marinus* DNA ligase, *Thermus scotoductus* DNA ligase, and *Bacillus stearothermophilus* DNA ligase.

18. The method of claim 1, wherein the DNA polymerase is a non strand-displacing DNA polymerase.

19. The method of claim 1, further comprising:
   introducing the DNA assembly product of step (b) into a host cell, and
   identifying a host cell that harbors the assembled circular DNA.

* * * * *